United States Patent [19]
Fleischmann

[11] Patent Number: 5,928,265
[45] Date of Patent: Jul. 27, 1999

[54] DEVICE FOR STIMULATING NEW TISSUE FORMATION IN TISSUE DEFECTS

[76] Inventor: Wim Fleischmann, Nelkenweg 15, D-89182 Bernstadt, Germany

[21] Appl. No.: 08/913,431

[22] PCT Filed: Mar. 29, 1996

[86] PCT No.: PCT/DE96/00608

§ 371 Date: Sep. 12, 1997

§ 102(e) Date: Sep. 12, 1997

[87] PCT Pub. No.: WO96/32073

PCT Pub. Date: Oct. 17, 1996

[30] Foreign Application Priority Data

Apr. 13, 1995 [DE] Germany .......................... 195 13 961

[51] Int. Cl.[6] .................................................. A61B 17/08
[52] U.S. Cl. ...................... 606/213; 606/216; 606/218
[58] Field of Search ..................................... 606/213, 214, 606/215, 216, 217, 218, 151, 148

[56] References Cited

U.S. PATENT DOCUMENTS 3,643,655   2/1972  Peronti .................................. 128/20
5,065,739  11/1991  Forrest et al. ............................ 128/20
5,263,971  11/1993  Hirshowitz et al. .................... 606/216
5,372,147  12/1994  Lathrop, Jr. et al. ................... 128/898
5,549,713   8/1996  Kim ......................................... 623/66
5,649,960   7/1997  Pavletic ................................. 606/216
5,733,305   3/1998  Fleischmann .......................... 606/213

FOREIGN PATENT DOCUMENTS 1210800  2/1986  U.S.S.R. ........................ A61B 17/02

*Primary Examiner*—Michael Buiz
*Assistant Examiner*—Tina T.D. Pham
*Attorney, Agent, or Firm*—Pendorf & Cutliff

[57] ABSTRACT

To stimulate the formation of new tissue in tissue defects, in addition to a constant distraction force, a periodically changing tractive force superimposed thereon is applied to the tissue regions adjacent to the tissue defect. To this end, a traction cable (12) holds the distraction means (10) arranged at the wound and is kept under traction at the other end. The traction cable (12) is deflected transversely by an eccentric (18) to generate the periodic tractive force.

14 Claims, 2 Drawing Sheets

DEVICE FOR STIMULATING NEW TISSUE FORMATION IN TISSUE DEFECTS

BACKGROUND OF THE INVENTION

The invention concerns a device for stimulation of new tissue formation.

Tissue distraction, in which a pull tension is exercised upon the tissue area bordering the tissue defects, is employed for accelerating the closure and healing of large surface area and deep tissue defects. It has been demonstrated that such a distraction force exercised upon the tissue leads to a more vigorous tissue proliferation and therewith to a more rapid closure of the wound.

DESCRIPTION OF THE INVENTION

This distraction force can be applied essentially along the plane of the tissue defect by a skin distractor (see for example U.S. Pat. No. 5 263 971). This has been found particularly advantageous in conjunction with large surface area skin defects with little depth. In large surface area defects with greater depth it is advantageous to apply an additional distraction force perpendicularly to the plane of the defect (see for example DE-GM 93 20 582). This vertical distraction force can either be applied via a pull force applied perpendicularly to a skin distraction device or thereby, that the wound is sealed vacuum tight by means of a foil and that a vertical pull force be applied upon the tissue under the foil.

SUMMARY OF THE INVENTION

The invention is concerned with the task of further improving tissue proliferation during skin distraction.

The invention is based on the realization, that tissue proliferation is beneficially influenced when the distraction force exercised upon the tissue is not maintained constant, but rather is varied periodically. The relative change in the introduced distraction force lies in the range of a few percentage or less. The duration of the distraction force change period lies thereby in a range of a few seconds or less. Beginning with this realization the invention provides a device, in which a periodically changing tension force is superimposed or transcribed upon the distraction force. This tension force which varies periodically preferably engages on those means, which are employed to exercise the distraction force, that is, preferably on the skin distracter or skin pinching device which is anchored on the edges of the wound, or on the vacuum seal which covers the wound.

It may be preferable that the additional periodic tension force is introduced via a traction cable, so that this tension force has an effect at an angle to the plane of the tissue defect. Depending on the manner of accomplishing the distraction effect, the periodic tension force can therewith have an angle of action of from 0° to 90° to the distraction force.

In a constructively simple embodiment which is advantageously installable upon the sick bed, a traction cable engages at the distraction means provided at the wound. The traction cable is maintained under tension and a periodic transverse deflection acting upon the traction cable produces the periodically varying tension force.

In order that during positional displacements of the patient, on the one hand, the traction cable is maintained under tension and, on the other hand, no undesirable additional tension forces are produced, measures are provided, so that the traction cable can follow the movements of the distraction means provided on the wound.

For this purpose, in one embodiment the traction cable is directed over a deflection pulley and a weight is provided at the end of the traction cable opposite to the distraction means. The weight keeps the traction cable under tension and follows positional changes of the patient by moving up and down. The weight produces thereby on the traction cable a constant pretension, which can be employed as the distraction force or as a partial component of the distraction force. This pre-tensioning can also be predetermined by changing the weights.

In order that a periodic transverse displacement of the traction cable is effected by a suitable periodic change of the tension force, the end of the traction cable must be held sufficiently securely by the weight. In the case of larger weights, that is, with a high pre-tensioning of the traction cable, the inertia of the weight is sufficient therefore. In the case of smaller weights, which correspond to a small pre-tensioning of the traction cable, an additional dampening measure is of advantage, so that the end of the traction cable cannot follow the transverse displacements. For this a fluid damper can be employed. Likewise, the traction cable can be guided over the deflection pulley for dampening in the manner of a band brake.

In a further embodiment the end of the traction cable opposite the distracter can be secured at a fixed mounting point. The traction cable is maintained under tension by a gas spring, whereby the gas spring permits change of position of the patient without change in the tension on the traction cable, however, a sufficient dampening is caused, so that the transverse displacement of the traction cable results in a varying distraction force.

BRIEF DESCRIPTION OF THE DRAWINGS

In the following, the invention will be described in greater detail by reference to the embodiments shown in the drawings. There are shown.

DETAILED DESCRIPTION OF THE INVENTION

Figure 1:
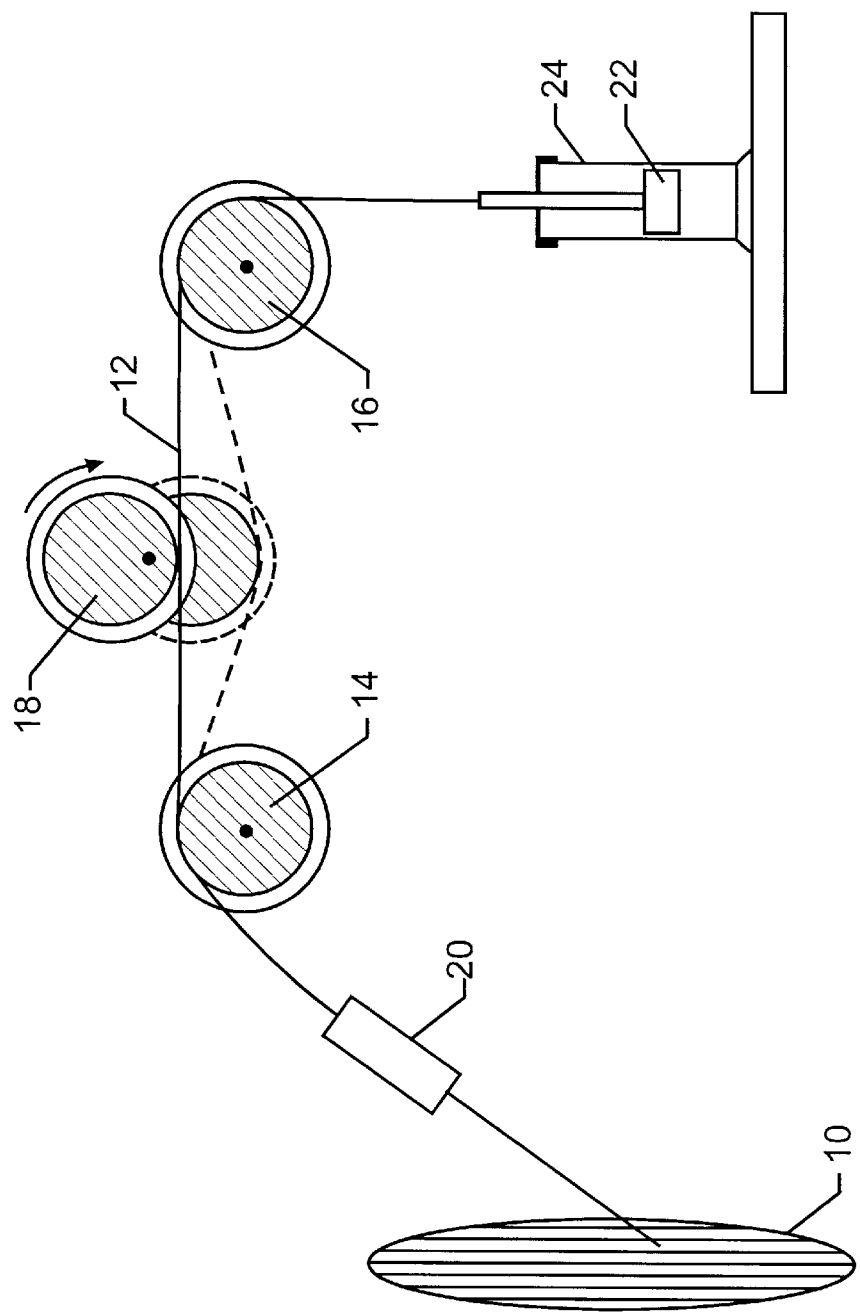
FIG. 1 a first embodiment of the device.

In the drawings the means for exercising the distraction force upon the tissue surrounding the tissue defect are only schematically represented and indicated with reference number 10. These means 10 for introduction of the distraction force could be a skin distractor or skin-pinching device anchored along the rim of the wound or a vacuum seal covering over the wound.

A traction cable 12 engages the distraction means 10 at an angle to the plane of the tissue defect. The traction cable 12 is tensioned via a rotatably mounted deflection roller 14 and a deflection pulley 16. Between the deflection roller 14 and the deflection pulley 16 an eccentric disk 18 with a circumferential notch rests against the traction cable 12. The eccentric disk 18 is driven by a not shown drive means with a rotational speed in the magnitude of approximately one revolution per second and deflects thereby in the transverse direction the traction cable 12 between the deflection roller 14 and the deflection pulley 16 which is maintained under tension, so that the pull force which is exercised via the traction cable 12 upon the distraction means 10 is periodically varied with the rotation of the eccentric disk 18.

The pull force exercised over the traction cable 12 upon the distraction means 10 can be measured with for example a pull force-measuring device 20, for example a spring scale incorporated in the traction cable 12, and thereby be measured and monitored.

Figure 2:
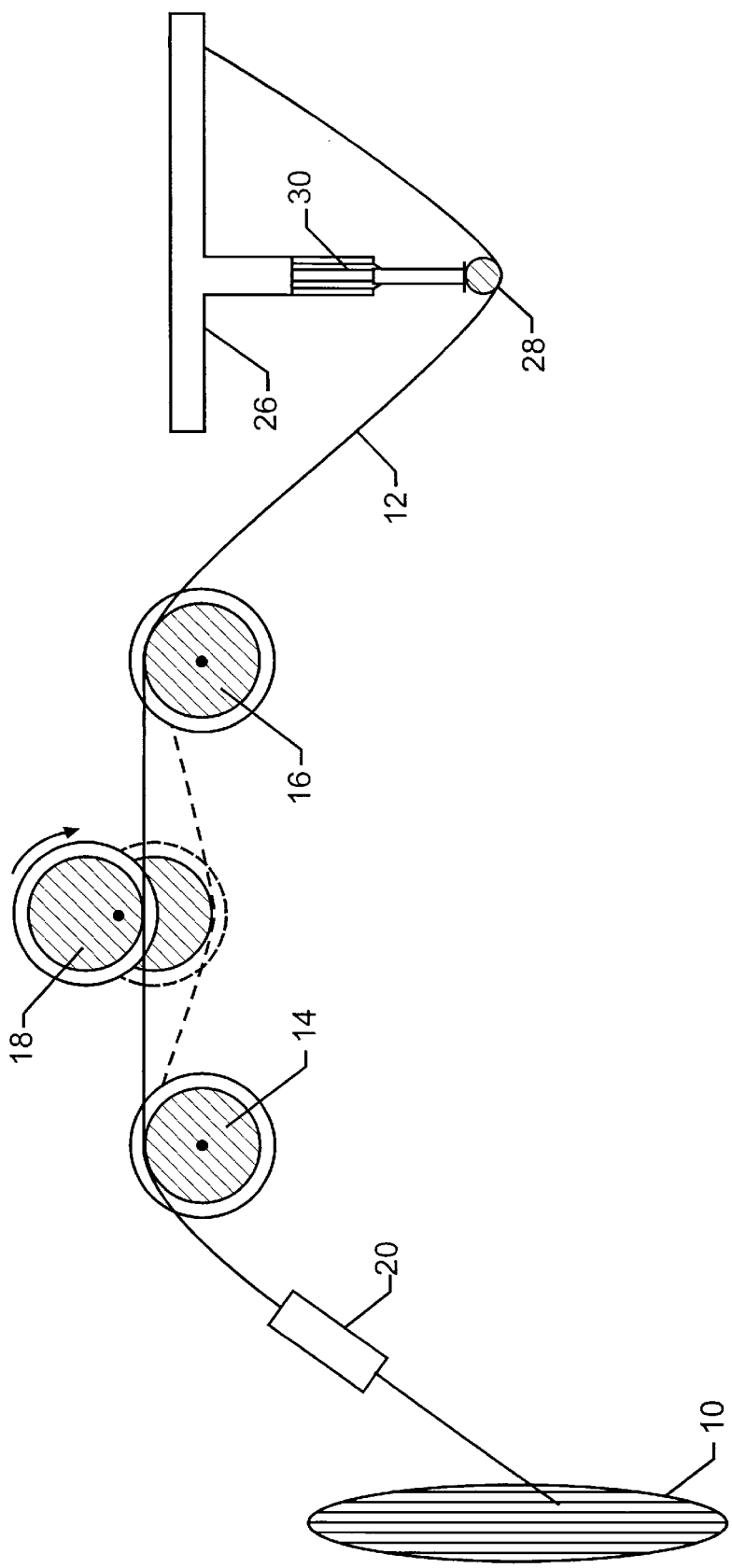
FIG. 2 a second embodiment of the device.

So far the exemplary embodiments according to FIG. 1 and FIG. 2 correspond to each other. The exemplary embodiments of FIG. 1 and 2 differ therein, in the manner in which the traction cable 12 is maintained under tension.

In the exemplary embodiment of FIG. 1 a weight 22 is provided at the end of the second free end of the traction cable 12 which is guided over the rotatably mounted deflection pulley 16. The weight 22 exercises in correspondence to its weight a constant pre-tensioning upon the traction cable 12, which exercises a constant distraction force via the distraction means 10. This pre-tensioning achieved by the weight 22 is periodically modulated by a tension force, which is accomplished by the transverse displacement of the traction cable 12 by means of the rotating eccentric disk 18.

In the case of a sufficiently large inertial mass of the weight 22 the weight 22 does not follow the rapid transverse deflection of the traction cable 12 by the eccentric disk 18 so that the second end of the traction cable 12 is maintained quasi-stationary by the weight 22 with respect to the periodic changing distraction force.

If the patient changes his bodily position, then also the distraction means 10 which is applied to the wound moves. This movement of the patient is accomplished slowly in comparison to the periodic pull force change exercised by the eccentric disk 18. The weight 22 can follow along with the relatively slow movement caused by the positional change of the patient, so that the traction cable 12 is maintained with constant pretension.

By the selection of the weight 22 the desired pre-tensioning or as the case may be the desired constant distraction force component can be maintained.

In order to prevent an oscillation movement of the weight 22, for example on the basis of the periodic effect of the force acting upon the traction cable 12 by the eccentric disk 18, the weight 22 can be guided vertically in a cylinder 24. In this case the weight 22 can be designed as a piston within the cylinder 24, so that a supplemental fluid dampening of the vertical movement of the weight 22 results. This fluid dampening, in addition of the inertial mass of the weight 22, supplementally prevents that the weight 22 follows the transverse movement of the traction cable 12 by the eccentric disk 18. Such a fluid dampening can be particularly of advantage, when only a small weight 22 is employed, in order that the traction cable 12 is provided with only a small pre-tensioning. If the cylinder 24 is filled with a dampening fluid, then there results a particularly strong dampening. Adjustable through-openings can be provided through the weight 22 functioning as a piston, in order to make the dampening effect adjustable.

In a variation of the embodiment of FIG. 1 a dampening of the vertical movement of the weight 22 can be thereby achieved, that the deflection pulley 16 is secured against rotation, so that the traction cable 12 runs with friction over the deflection pulley 16 in the manner of a band brake. The frictional rubbing of the traction cable 12 upon the outer circumference of the deflection pulley 16 prevents thereby that the free end of the traction cable 12 with the weight 22 can follow the rapid transverse displacements of the traction cable 12 by the eccentric disk 18. The amount or magnitude of the braking can be determined and improved by appropriately coating the outer circumference of the deflection pulley 16 as well as by the suitable selection of the material of the traction cable 12.

In this embodiment it has been found to be of advantage, that during the transverse displacement of of the traction cable 12 shown in the drawing by broken lines this is applied over a greater arc along the outer circumference of the deflection pulley 16, so that the rubbing resistance is increased.

The circumference of the deflection pulley 16 could also, in this embodiment, be provided with a friction increasing outer surface or coating over an arc or segment thereof. In this manner, by rotating the deflection pulley 16, a greater or lesser segment of the deflection pulley 16 which is provided with the frictional increasing coating comes into contact with the traction cable 12. Thereby the frictional resistance, and therewith with the dampening effect, is adjustable.

In the embodiment shown in FIG. 2 the second end of the traction cable 12, the opposite end to the distraction means 10, is attached securely and fixedly to a frame 26 of the device. Between the frame 26 and the rotatably mounted deflection pulley 16 the traction cable 12 is guided over a roller 28 which is attached to a gas pressure spring 30 attached to the frame 26. The gas pressure spring 30 keeps the traction cable 12 under tension with a pre-determined tension as corresponds to its spring pressure.

During a positional movement of the patient the traction cable 12 can follow the movement of the distraction means 10 in that the gas pressure spring 30 is moved telescopically inward or outwards. The pre-tension exercised upon the traction cable 12 by the gas pressure spring 30 does not change as a result spring characteristic of the gas pressure spring 30.

The dampening of the gas pressure spring 30 is however sufficiently large, that the gas pressure spring 30 cannot follow the rapid transverse deflection of the traction cable 12 by the eccentric disk 18. With respect to the periodic change of the tension force by the eccentric disk 18, the end of the traction cable 12 is maintained quasi-stationary via the gas pressure spring 30.

What is claimed is:

1. Device for stimulation of new tissue formation in tissue defects, said device comprising:

tissue distractor means for exercising a distraction force upon the tissue area bordering the tissue defect, and means for superimposing a modulating tension force upon the distraction force by adding a pull force component, of which the magnitude automatically changes periodically.

2. Device according to claim 1, wherein said pull force component of which the magnitude changes periodically is applied directly to the distractor means (10).

3. Device according to claim 2, wherein the distraction force is applied to the distraction means (10) via a traction cable (12).

4. Device according to claim 3, further comprising compensation means such that the distraction means (10) can be moved without changing the pretension component of the traction cable (12).

5. Device according to claim 4, further comprising means for dampening the movement of said traction cable (12).

6. Device according to claim 3, wherein the traction cable (12) applies a pretension which is modulated by a periodic pull force, which pull force comprises at least a partial component of the distraction force.

7. Device according to claim 6, wherein said traction cable (12) has a first end and a second end, wherein said first end is provided at the distraction means (10), wherein said second end is secured to a attachment point (22, 26), said device further comprising means for applying a relatively constant pretension to said traction cable (12), and comprising means for generating a modulating pull force by a periodic transverse deflection of the traction cable (12), further comprising compensation means such that the distraction means (10) can be moved without changing the pretension component of the traction cable (12), wherein the second end of the traction cable is guided over a deflection pulley (16) and attached to a weight (22) as a counter attachment point.

8. Device according to claim 7, further comprising means for dampening the movement of said traction cable (12), wherein said dampening is accomplished by dampening the movement of the weight (22).

9. Device according to claim 8, wherein the movement of the weight (22) is damped by a fluid dampening means (24).

10. Device according to claim 7, wherein the traction cable (12) runs over the deflection pulley (16) as a band friction dampening means.

11. Device for stimulation of new tissue formation in tissue defects, said device comprising:

tissue distractor means for exercising a distraction force upon the tissue area bordering the tissue defect, and means for modulating the distraction force by adding a pull force component, of which the magnitude changes periodically, wherein said pull force component of which the magnitude changes periodically is applied directly to the distractor means (10), wherein the distraction force is applied to the distraction means (10) via a traction cable (12), and wherein said traction cable (12) has a first end and a second end, wherein said first end is provided at the distraction means (10), wherein said second end is secured to a attachment point (22, 26), said device further comprising means for applying a relatively constant pretension to said traction cable (12), and comprising means for generating a modulating pull force by a periodic transverse deflection of the traction cable (12).

12. Device according to claim 11, wherein the transverse deflection is caused by an eccentric (18) which engages the traction cable (12).

13. Device according to claim 11, further comprising compensation means such that the distraction means (10) can be moved without changing the pretension component of the traction cable (12), further comprising means for dampening the movement of said traction cable (12), wherein the second end of the traction cable (12) is attached to a fixed attachment point (26) and wherein said compensation means for maintaining the traction cable (12) under relatively constant tension is a gas pressure spring (30).

14. Device for stimulation of new tissue formation in tissue defects, said device comprising:

tissue distractor means for exercising a distraction force upon the tissue area bordering the tissue defect, and means for modulating the distraction force by adding a pull force component, of which the magnitude changes periodically, wherein said pull force component of which the magnitude changes periodically is applied directly to the distractor means (10), wherein the distraction force is applied to the distraction means (10) via a traction cable (12), and wherein the traction cable (12) is provided with a tension force measuring device (20).

* * * * *